(12) United States Patent
Dyall

(10) Patent No.: US 10,226,596 B1
(45) Date of Patent: Mar. 12, 2019

(54) CATHETER AND GUIDEWIRE ADVANCEMENT DEVICE

(71) Applicant: Bowline Medical Pty Ltd, Albert Park, Victoria (AU)

(72) Inventor: Andrew Dyall, Victoria (AU)

(73) Assignee: Bowline Medical Pty Ltd, Albert Park, Victoria (AU)

( * ) Notice: Subject to any disclaimer, the term of this patent is extended or adjusted under 35 U.S.C. 154(b) by 0 days.

(21) Appl. No.: 16/122,856

(22) Filed: Sep. 5, 2018

(51) Int. Cl.
*A61M 25/01* (2006.01)
*A61J 15/00* (2006.01)

(52) U.S. Cl.
CPC .......... *A61M 25/01* (2013.01); *A61J 15/0003* (2013.01); *A61M 25/0113* (2013.01)

(58) Field of Classification Search
CPC . A61M 25/01; A61M 25/0113; A61J 15/0003
See application file for complete search history.

(56) References Cited

U.S. PATENT DOCUMENTS

| | | |
|---|---|---|
| 3,683,928 A | 8/1972 | Kuntz |
| 4,838,880 A | 6/1989 | Honma |
| 5,569,159 A | 10/1996 | Anderson et al. |
| 8,728,057 B2 | 5/2014 | House |
| 2003/0158561 A1 | 8/2003 | Kanesaka |
| 2009/0137986 A1 | 5/2009 | Golden et al. |
| 2010/0072441 A1 | 3/2010 | Haslacher |
| 2012/0041260 A1 | 2/2012 | Yamada |
| 2012/0253320 A1* | 10/2012 | Steegers ............... A61M 25/01 604/528 |
| 2014/0066905 A1 | 3/2014 | Young |
| 2017/0043136 A1 | 2/2017 | Nichols |

FOREIGN PATENT DOCUMENTS

| | | |
|---|---|---|
| EP | 2433670 A1 | 3/2012 |
| GB | 2535973 A | 9/2016 |
| WO | WO89/000409 A1 | 1/1989 |
| WO | WO03/008028 A2 | 1/2003 |
| WO | WO03/051447 A1 | 6/2003 |

* cited by examiner

*Primary Examiner* — Amber Stiles
(74) *Attorney, Agent, or Firm* — Shay Glenn LLP

(57) ABSTRACT

A catheter advancement device to assist with the ease and sterility of insertion of catheters and other elongate, flexible medical devices is disclosed. It includes two one-way valves that may be reciprocated with respect to each other. Some variations may include a demount gap which may be continuously opened or may be controllable opened and closed.

22 Claims, 19 Drawing Sheets

8

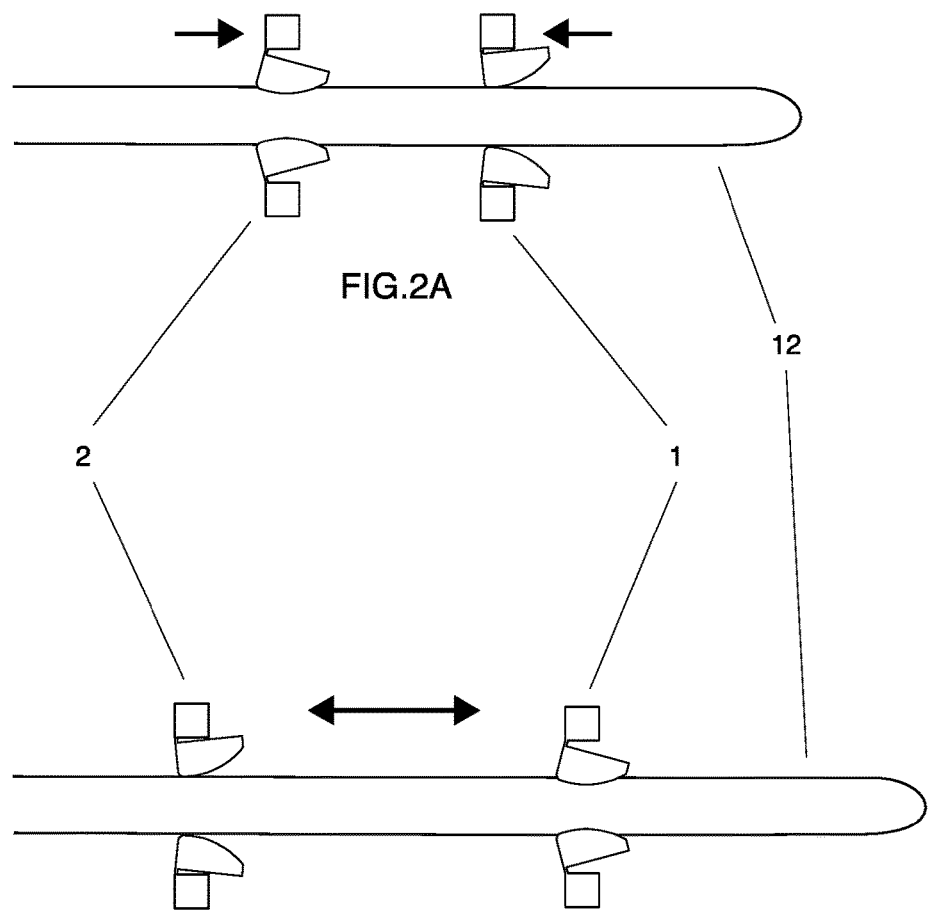

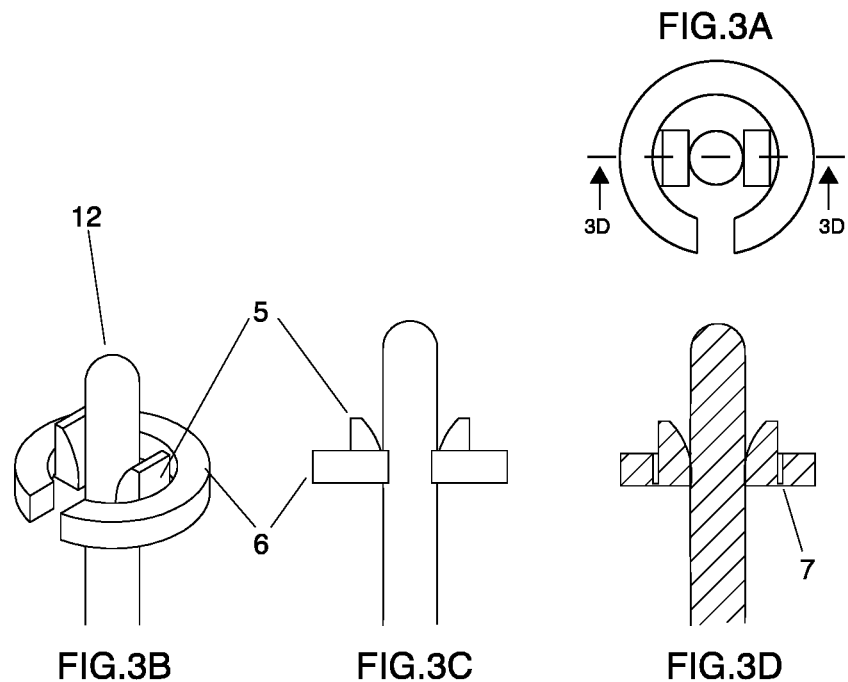
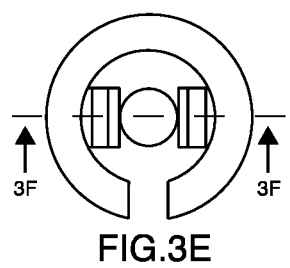
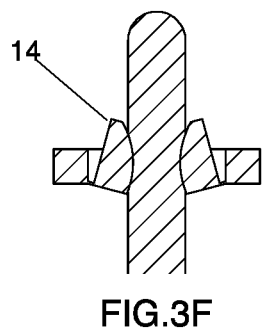

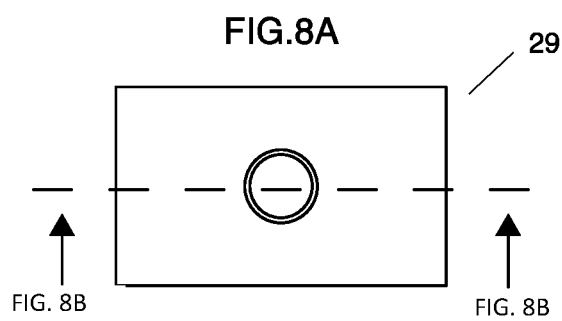
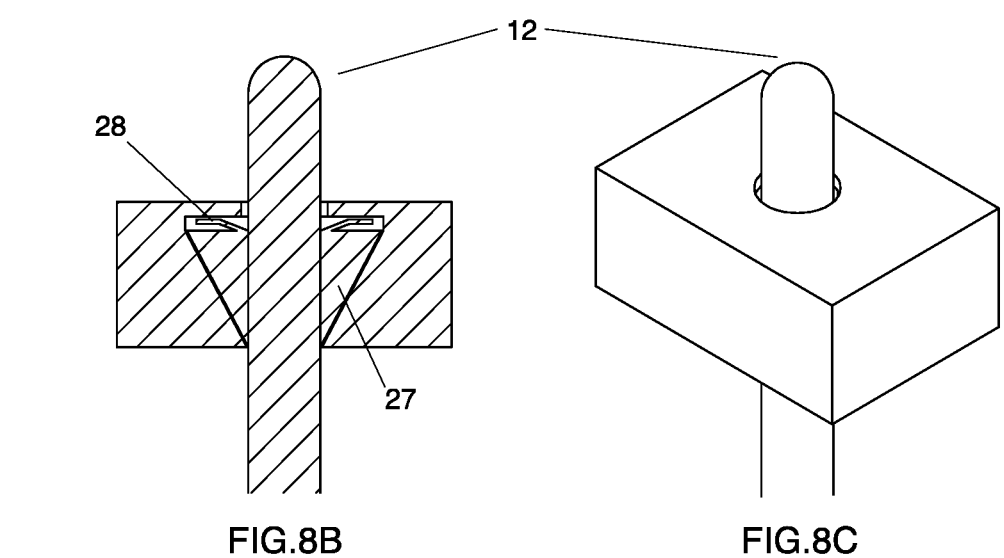

FIG.9A
FIG.9B
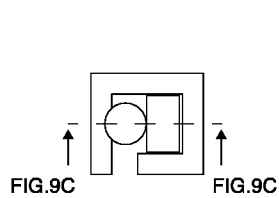
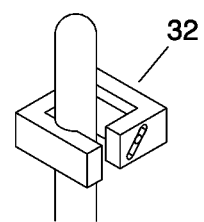
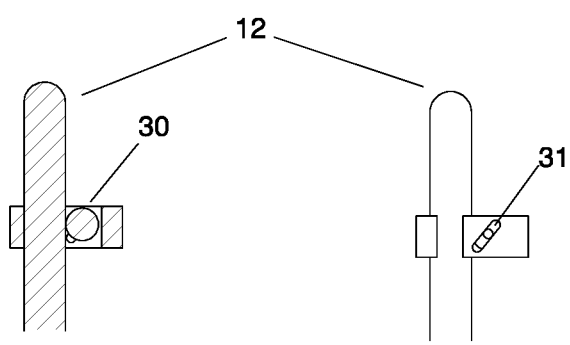
FIG.9C
FIG.9D

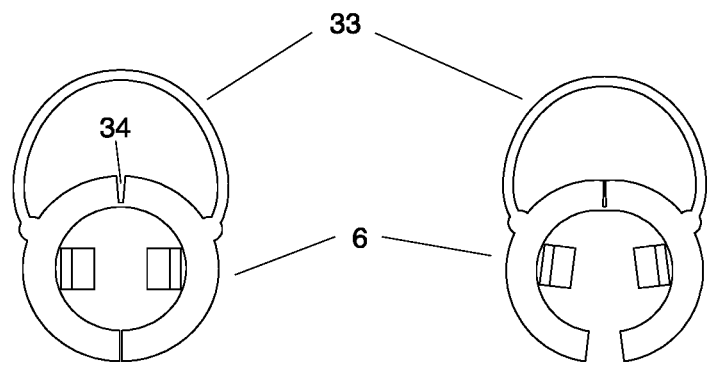
FIG.10A  FIG.10B
FIG.11A
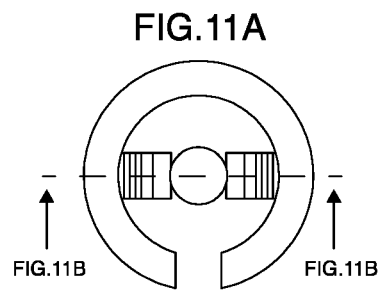
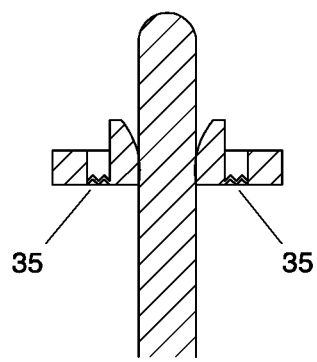
FIG.11B

FIG.24A
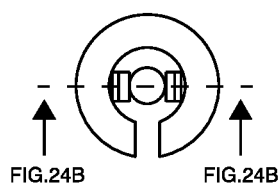
FIG.24B         FIG.24B
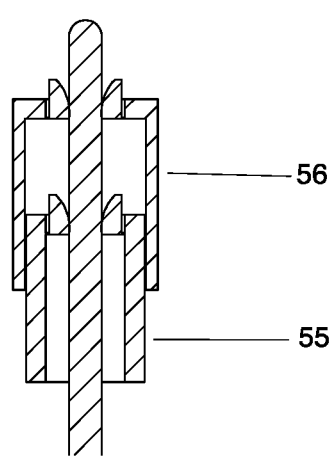
— 56
— 55
FIG.24B
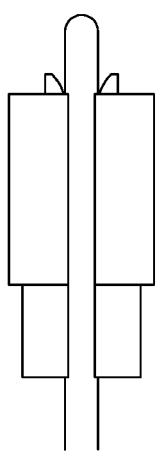
FIG.24C
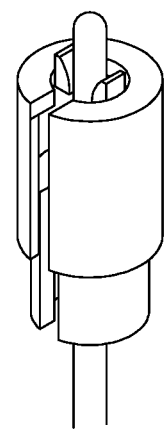
FIG.24D

CATHETER AND GUIDEWIRE ADVANCEMENT DEVICE

CROSS REFERENCE TO RELATED APPLICATIONS

This patent application claims priority to Australian Provisional Patent Application no. 2017903585, filed on Sep. 5, 2017, and titled ("CATHETER AND GUIDEWIRE ADVANCEMENT DEVICE") which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relate generally to medical devices to assist in the advancement of a catheter and/or guidewire.

BACKGROUND

Catheters are routinely used in medicine for access to body spaces such as the urinary bladder, blood vessels, and portions of the biliary tree or abdominal or thoracic cavity. They are used mainly for monitoring, drainage and for infusion of fluids.

Especially where the insertion of a catheter involves piercing of other tissues, the Seldinger technique is frequently used for insertion. This involves gaining access to the body space with a hollow needle, advancement of a guidewire through the hollow part of the needle into the space, removal of the needle and then advancement of a catheter over the guidewire followed by removal of the guidewire. In other circumstances, such as the insertion of a urinary catheter through the urethra and into the bladder, catheters may be inserted without the use of a guidewire.

Any procedure involving cannulation of a body part entails the risk of infection. If aseptic technique is not adhered to, infection risks are greater. This is particularly so when placing central venous catheters, and is widely held to be true also for urinary catheters. Although sterile gloves are usually worn during insertion of catheters and guidewires, these can become contaminated. The operator may be unaware of this. A system, therefore, which does not involve touching objects which are inserted into the body would therefore be preferable.

Catheters and guidewires are elongated and in most cases their purpose mandates flexibility. This flexibility presents challenges for applying the necessary axial force for them to overcome the tissues' resistance to insertion and advancement without buckling of the catheter. The tendency to buckle can be mitigated by decreasing the distance between the point at which force is exerted on the catheter and the point at which resistance is encountered, by internal or external stiffeners or guides, or both. The needle through which a guidewire is inserted in the Seldinger technique serves as an external stiffener as well as to guide it to the correct place. Insertion of a urinary catheter requires repeated gripping of the catheter close to the urethral orifice, advancement by small distances and repeated repositioning of the grip.

A recent advance in the insertion of catheters and cannulas is the use of ultrasound for visualization of the relevant anatomy and to guide the insertion process. This involves the use of ultrasound gel on the skin at the site of insertion. This gel is slippery and makes the gripping and advancement of both guidewires and catheters prone to slippage and therefore more difficult. Gel may also be used as a lubricant for the insertion of a catheter, for example in the insertion of urinary catheters, with similar problems.

In the case of the insertion of central venous catheters, the common means for advancement of the guidewire involves pushing it with gloved digits along its path. For insertion of a urinary catheter, the urethral orifice is held steady and accessible with one hand whilst the lubricated catheter is fed into the orifice with the other. The procedure should not involve touching the catheter. It would ideally be pushed out of a perforated, sterile pouch which is split gradually along its length as the catheter is inserted. This is a difficult technique to master with one hand and even experienced health care practitioners frequently abandon the sterile pouch and feed the catheter manually.

In the case of insertion of a nasogastric tube (NGT) in an unconscious patient, the NGT is fed through one of the patient's nostrils into the nasopharynx and thence into the pharynx. At this point it is usually necessary to insert forceps through the patient's mouth into the pharynx in order to grip the NGT and advance it into the esophagus. Because of the limited space it is usually necessary to grip, advance and release the NGT many times. The NGT is frequently difficult to feed in this manner as it has a tendency to flex at points of resistance to advancement, then recoil to its original position when the grip is released.

For the insertion of both urinary and central venous catheters, a technique or device which obviates the need for manual handling of the catheter and/or guidewire would make the task easier, quicker and, in theory, reduce the risk of infection. For the insertion of NGT's, a device which could advance an NGT in the pharynx without allowing the NGT to recoil distally would be advantageous.

Intermittent urinary self-catheterization is performed by patients with poorly functioning bladders and/or urinary incontinence. In this procedure a patient inserts a catheter through their urethra to empty their bladder when it requires emptying. It causes fewer urinary infections than a long-term urinary catheter but some patients are unable to perform the procedure because of limited dexterity. A device which makes the procedure easier would allow more patients to self-catheterize and lower their likelihood of developing urinary infections.

Many catheters comprise, at their distal ends, drainage or infusion ports which are greater in diameter than the shafts of their respective catheters. In order to demount an advancement device from the catheter, it should either have sufficient internal diameter to allow for the size of said ports, or allow for demounting laterally so as to avoid said ports.

SUMMARY OF THE DISCLOSURE

Described herein are apparatuses (including systems, devices, tools, etc.) and methods for advancing a catheter with one hand without the need to touch the catheter manually. The apparatuses and methods described herein may significantly help with the insertion of flexible, elongate medical devices, including but not limited to catheters and guidewires, particularly during a surgical procedure and/or in the presence of a lubricious material. Typically such flexible elongate medical devices may be difficult to insert and advance by reason of their shape and flexibility. They ideally should be inserted without touching them, even with gloves, to minimize the chance of infection. Where one hand is utilized to steady the target anatomy, as in the insertion of a urethral catheter, the procedure is challenging and often leads to compromised sterility.

The methods and apparatuses described herein are configured to advance a flexible, elongate medical device (e.g., a catheter or guidewire) without the need for manual handling of the flexible elongate medical device. These apparatuses can be operated by one hand and even, in some variations, be operated whilst the apparatus is inside a sterile pouch. The methods and apparatuses described herein may offer a faster performance, such as during the application of a catheter (e.g., catheterization) or insertion of guidewire, with less prolongation of the discomfort of the procedure. These methods and apparatuses may also provide for easier procedure with less chance of contamination of the catheter.

In general, these apparatuses may include an advancement device for advancing an elongate flexible medical device (such as, but not limited to, a catheter). The device may include: a first one-way gripping valve at the distal end of a first arm having a first opening configured to hold the elongate flexible medical device; a second one-way gripping valve at the distal end of a second arm having a second opening configured to hold the elongate flexible medical device; and a hinge region connecting the first arm to the second arm at an angle of between 10 degrees and 180 degrees; wherein the hinge region is configured to allow the angle between the first arm and the second arm to change to reciprocate the first one-way gripping valve and the second one way gripping valve to advance the elongate flexible medical device.

Although the devices and methods of using them described herein may be referred to as "advancement devices" it should be clear that they may be used to move an elongate flexible member such as a catheter forwards or in the opposite direction (e.g., reverse). Thus, an "advancement device" may advance an elongate flexible medical device (e.g., catheter, guidewire) towards a patient in a first orientation to insert the flexible medical device, or away from the patient if used in the second orientation to remove the flexible medical device.

For example, described herein are catheter advancement devices comprising: a first one-way gripping valve at the distal end of a first arm, wherein the first one-way gripping valve is configured to allow a catheter to move in a first direction through an opening of the first one-way gripping valve while preventing the catheter from moving in a second direction that is opposite from the first direction; a second one-way gripping valve at the distal end of a second arm, wherein the second one-way gripping valve is configured to allow the catheter to move in the first direction through an opening of the second one-way gripping valve while preventing the catheter from moving in the second direction; and a hinge region connecting the first arm to the second arm at an angle so that the opening of the first one-way gripping valve is approximately coaxially the opening of the second one-way gripping valve; wherein the hinge region is configured to allow the first arm to move relative to the second arm to reciprocate the one-way gripping valve and the second one way gripping valve to advance the catheter.

A catheter advancement device may include: a first one-way gripping valve at the distal end of a first arm, wherein the first one-way gripping valve is configured to allow a catheter to move in a first direction through an opening of the first one-way gripping valve while preventing the catheter from moving in a second direction that is opposite from the first direction; a second one-way gripping valve at the distal end of a second arm, wherein the second one-way gripping valve is configured to allow the catheter to move in the first direction through an opening of the second one-way gripping valve while preventing the catheter from moving in the second direction; a living hinge region connecting the first arm to the second arm at an angle of between 10 degrees and 180 degrees; wherein the hinge region is configured to allow the angle between the first arm and the second arm to change to reciprocate the first one-way gripping valve and the second one way gripping valve to advance the catheter; a first demount gap in the first one-way gripping valve through which the catheter may demount from the first one-way gripping valve; and a second demount gap in the second one-way gripping valve through which the catheter may demount from the second one-way gripping valve.

Any of the devices described herein may include a demount gap in at least one of the first one-way gripping valve and the second one-way gripping valve, through which the catheter may demount from the device. For example, the demount gap may comprise a gap formed in a frame partially surrounding the first one-way gripping valve. The demount gap may be gated. For example, the device may include a gate configured to be opened or closed to open or close the demount gap. Thus, any of these devices may include a gate actuator configured to open or close the gate via a control coupled to one or both of the first and second arms.

In general, any of these devices may be hand operated, by using a single hand. In some variations the device may include a grip region. For example, the first arm and the second arm may be configured as or may include a grip region. The grip region may include a depression and may be textured to improve grip. In some variations the grip region may include one or more loops to engage one or more fingers or thumb.

Any of these variations may include a third arm connected to the first one-way gripping valve, a fourth arm connected to the second one-way gripping valve, and a second hinge region connecting the third arm to the second arm.

In general, the hinge region may connect the first arm to the second arm at an angle, e.g., of between 5 degrees and 185 degrees (e.g., 10 degrees and 180 degrees, 10 degrees and 180 degrees, 15 degrees and 175 degrees, 20 degrees and 160 degrees, 5 degrees and 60 degrees, 5 degrees and 50 degrees, 5 degrees and 45 degrees, etc.).

Any appropriate one-way gripping valve may be used for the first and/or second one-way gripping valves and the second one-way gripping valve. For example, the one-way gripping valves may each comprises one or more cams (e.g. 2 cams, 3 cams, etc.).

In general, the hinge region may connect the first arm to the second arm so that the opening of the first one-way gripping valve is coaxially with the opening of the second one-way gripping valve (e.g., within +/−30 degrees of the opening of the second one-way gripping valve, within +/−25 degrees of the opening of the second one-way gripping valve, within +/−20 degrees of the opening of the second one-way gripping valve, within +/−15 degrees of the opening of the second one-way gripping valve, etc.). The opening of the first one-way gripping valve may be coaxially with the opening of the second one-way gripping valve so that the catheter may extend through both openings in a straight, or substantially straight, line. In some variations, the hinge region comprises a living hinge. A living hinge may refer to a hinge formed of a continuous material, e.g., a thin flexible hinge or flexure bearing that may be made from the same material as the two pieces it connects, rather than some other flexible substance. It may be thinned or cut to allow the pieces to bend along the line of the hinge.

Any of the devices described herein may include a guide enclosure extending from the first one way gripping valve, towards the second one-way gripping valve to inhibit buckling of the catheter during advancement. More than one guide enclosure may be used. The guide enclosure may help prevent kinking or bending of the elongate flexible device (e.g., catheter) between the first and second one-way gripping valves.

In some variations, the apparatus may include two valves, (which may or may not be of the same design), disposed coaxially or approximately coaxially with respect to each other; a reciprocation mechanism causing said two valves to move with respect to each other, alternating an 'approximation phase' during which the two valves come closer to each other, and a 'distancing phase', during which the two valves move away from each other. In both phases, the two valves substantially maintain their coaxial relationship with each other and with the catheter; and a demount gap in the valve frames for mounting and demounting the catheter or guidewire onto the device. Said demount gap may be permanent, may be created by breaking open the frame at a weak point, or may open and/or close at a hinge. The opening and closing of said demount gap and/or the maintenance of the open and/or closed state of said valves by pivoting around said hinge may be effected by a latch or biasing mechanism and may be operated at a distance from the valve, especially in circumstances in which there is insufficient space for the operator's fingers to operate close to the valve. Permanent demount gaps in respective valves may be angularly offset from each other so as to allow demount of the catheter only when said valves are axially rotated with respect to each other in a way which aligns said permanent gaps in their respective valve frames.

The reciprocation mechanism may further comprise a living hinge which can be injection molded in an open position, then flexed after injection molding into the functional position, in which the valves are substantially coaxial. Said reciprocation mechanism with living hinge may further comprise a latch mechanism which prevents unfolding of the hinge and also biases the valves away from each other.

In some variations, e.g., designed for intermittent catheterization, the device may include: two valves, (which may or may not be of the same design), disposed coaxially or approximately coaxially with respect to each other; and a reciprocation mechanism causing the two valves to move with respect to each other, alternating an 'approximation phase' during which the two valves come closer to each other, and a 'distancing phase', during which the two valves move away from each other. In both phases, the two valves substantially maintain their coaxial relationship with each other and with the catheter. Said reciprocation device further comprises a living hinge which can be injection molded in an open position, then flexed after injection molding into the functional position, in which the valves are substantially coaxial. Said reciprocation device with living hinge may also comprise a latch mechanism which prevents unfolding of the hinge and also biases the valves away from each other.

Any of the above embodiments may further comprise an anti-buckling mechanism, which inhibits flexion or buckling of the portion of catheter or guidewire located between the two valves.

Also described herein are methods of operating any of the advancement devices to advance an elongate flexible member such as a catheter. For example, described herein are methods of advancing a catheter using a hand-held catheter advancement device having a first one-way gripping valve at the distal end of a first arm, a second one-way gripping valve at the distal end of a second arm, and a hinge region connecting the first arm to the second arm, the method comprising: compressing the hinge region to reduce the angle between the first arm and the second arm, so that the first one-way gripping valve moves along the catheter in a first direction while the second one-way gripping valve grips onto the catheter; and expanding the hinge region to increase the angle between the first arm and the second arm, so that the first one-way gripping valve grips the catheter while the second one-way gripping valve moves along the catheter in the first direction; thereby moving the catheter in a second direction that is opposite to the first direction.

Any of these methods may include releasing the catheter from the hand-held catheter advancement device by pulling the catheter out of the a first demount gap in the first one-way gripping valve and by pulling the catheter out of a second demount gap in the second one-way gripping valve.

The catheter (or other elongate, flexible medical device) may be released from the advancing device by activating a control on one or both of the first and second arms to open a first gate closing the first demount gap.

In any of these methods, the catheter may first be attached into the first and second one-way gripping valves.

The first and second arms and the hinge may be biased to open or to close. For example, compressing the hinge region may comprise pushing the first arm and the second arm towards each other, further wherein expanding the hinge region comprises releasing the first arm and the second arm to self-expand; alternatively, compressing the hinge region may comprise allowing the first arm and the second arm to move towards each other, further wherein expanding the hinge region comprises pulling the first arm and the second arm apart from each other. In some variations, compressing the hinge region comprises pushing the first arm and the second arm towards each other, and expanding the hinge region comprises pulling the first arm and the second arm apart from each other. The steps of compressing and expanding may be done one-handed.

Any of these methods may include operating the device through a sterile field (e.g. through a sterile bag). For example, the method may include compressing the hinge region comprises compressing the hinge region through a sterile bag.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A and 2B illustrate one example of how an advancement device such as the one shown in FIGS. 1A-1E may operate to reciprocate two one-way gripping valves and result in proximal movement of a catheter with respect to the advancement device. FIG. 2A is a view of the approximation phase. FIG. 2B is a view of the distancing phase.

FIG. 3A is a plan view of an embodiment of a one-way gripping valve in which there are two cams. The valve is shown in the relaxed state.

FIG. 3B is a perspective view of the valve of FIG. 3A in which there are two cams. The valve is shown in the relaxed state.

FIG. 3C is a side view of the one-way gripping valve of FIG. 3A in which there are two cams. The valve is shown in the relaxed state.

FIG. 3D is a cross-sectional view of the valve of FIG. 3A in which there are two cams. The valve is shown in the relaxed state.

FIGS. 3E and 3F are plan and cross-sectional views, respectively, of the valve of FIG. 3A shown in the gripping state.

FIG. 4A is a plan view and FIG. 4B is a cross-sectional view.

FIGS. 8A to 8C are plan, cross-sectional and perspective views, respectively, of an embodiment of a valve in which the catheter-contact elements are spring-biased sliding plugs.

FIGS. 9A to 9D are plan, isometric, cross-sectional and elevation views, respectively, of an embodiment of a valve in which a sloping roller mechanism either engages or disengages with a catheter depending on whether the catheter is moving distally (e.g., away from) or proximally (e.g., towards) with respect to the valve, respectively.

FIGS. 10A and 10B are plan views of an embodiment of a one-way gripping valve in which the force of contact between the catheter contact surfaces and the catheter is increased by a spring which biases the catheter-contact members of the valve into contact with the catheter. In FIG. 10A the spring is illustrated in its relaxed state and the valve is closed. In FIG. 10B the valve is illustrated in its open-most state and the spring is flexed.

FIGS. 11A and 11B are plan and cross-sectional views of an embodiment of a one-way gripping valve in which the force of contact between the valve and the catheter is increased with springs biasing the catheter-contact surfaces in a centripetal direction.

In FIG. 12A the one-way gripping valves are open, and in FIG. 12B the valves is closed. In some variations the valves may be separately operated (open/closed).

FIG. 18A is a perspective view in the fully open state. FIG. 18B is a plan view in the fully open state. FIG. 18C is a section view in the fully open state. FIGS. 18D and 18E are perspective and cross-sectional views of the mechanism as it is folded towards the functional state. FIGS. 18F and 18G are perspective and cross-sectional views of the mechanism in the functional state.

FIGS. 24A to 24D are plan, cross-sectional, elevation and isometric views, respectively, of an embodiment of an anti-buckling mechanism, configured as an anti-buckling enclosure, for a hand-operated catheter advancement device in which the portion of the catheter temporarily between the two valves is prevented from buckling by being enclosed within an enclosure, shown as a cylinder, or partial-cylinder in this example.

DETAILED DESCRIPTION

Figure 1A:
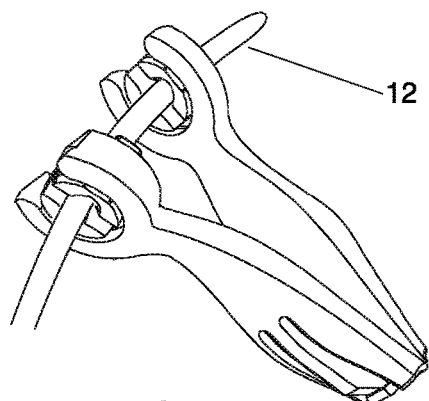
FIG. 1A is a perspective view of one embodiment of an apparatus, configured to aid in inserting a urinary catheter. The device is shown acting on an exemplary mounted urinary catheter. This device may be referred to as a hand-operated catheter advancement device.
Figure 1B:
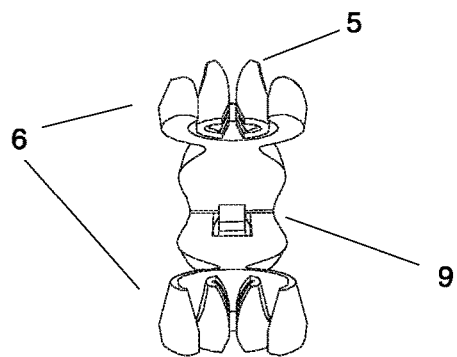
FIG. 1B is a front elevation view of the device of FIG. 1A.

Methods and apparatuses for advancing an elongate, flexible medical device (such as a catheter, guidewire, or the like) are described. In particular, described herein are apparatuses (e.g., devices) for advancing an elongate flexible medical device that include a pair of one-way gripping valves that are connected by a pair of arms and a hinge region. Moving the flexible arms (e.g., bending at the hinge region) may reciprocate the first and second one-way gripping valves (which, for convenience, may be referred to herein as simply 'valves'). The one-way gripping valves are configured to allow an elongate flexible member (such as a catheter) to move in a first direction through an opening (e.g., a channel) of the one-way gripping valve, while preventing the elongate flexible member from moving in a second direction that is opposite from the first direction. The hinge region may be configured to allow the first arm to move relative to the second arm to reciprocate the one-way gripping valves to advance the catheter. In some variations these apparatuses may include one or more demount gaps in the one-way gripping valves through which the elongate flexible device may demount from the advancing device (e.g., from each of the one-way gripping valves).

For clarity and to avoid repetition the usage of some terms in this document is clarified. For example, 'catheter' in the singular and plural may refer to catheters, guidewires and other elongate, flexible medical devices. As will be apparent from the context, 'proximal' and 'distal' may be used to describe the relative location on the device (e.g., distal may refer to distal from the hinge region, while proximal may be at the opposite end of the device). In some variations, proximal and distal may refer to the patient's point of view, so that the proximal tip of the catheter is the first to enter the patient. 'Centripetal' is the direction towards the axis of the catheter or valve (e.g., radially inward). 'Centrifugal' is the direction away from the axis of the device or catheter (e.g., radially outward).

'Valve' refers to a part of the apparatus which allows movement of the catheter along the catheter's axis in one direction but inhibits movement in the opposite direction. For insertion of a catheter into a patient, the direction of movement is proximal. The valves described herein may be referred to as one-way gripping valves, and may include camming valves (or half-camming valves), and the like.

Two states of the valve are described: the 'gripping' and the 'relaxed' states. In the 'gripping' state the valve is impeding distal movement of the catheter with respect to said valve. In the 'relaxed' state the valve is allowing proximal movement of the catheter with respect to said valve. The axis of the valve is coincident with the catheter's axis when it is mounted in the apparatus.

The 'nip' of a valve is the space in the valve through which the catheter may pass, between the catheter-contact surfaces.

Some embodiments of valves allow for 'open' and 'closed' states. In the 'open' state, the valve frame is open in the sense that the catheter can be mounted in this state, but the valve is otherwise non-functional. The 'closed' state is that state in which the valve is functional but does not allow mounting or demounting of the catheter. 'Reciprocal motion' of the valves is the alternating movement of the valves towards each other and away from each other in what is called, in this document, the 'approximation' and 'distancing' phases respectively. Reciprocal motion may be linear, arcuate, or approximately so.

'Advancement', when used to describe the motion of a catheter, means movement of said catheter in the desired direction along its axis. Where a demount mechanism or feature is described for removal of a catheter from the device, it may also allow mounting of a catheter into the device.

The apparatuses (e.g., devices) described herein may be operated as a tool for assisting with the placement into the body of a catheter or other elongated, flexible medical device.

Figure 1C:
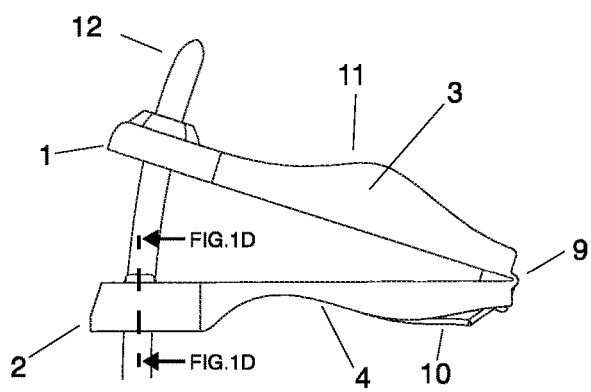
FIG. 1C is a side elevation view of the device of FIG. 1A.
Figure 1D:
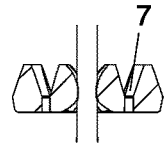
FIG. 1D is a cross-sectional view of FIG. 1C through a one-way gripping valve on a distal region of the device.
Figure 1E:
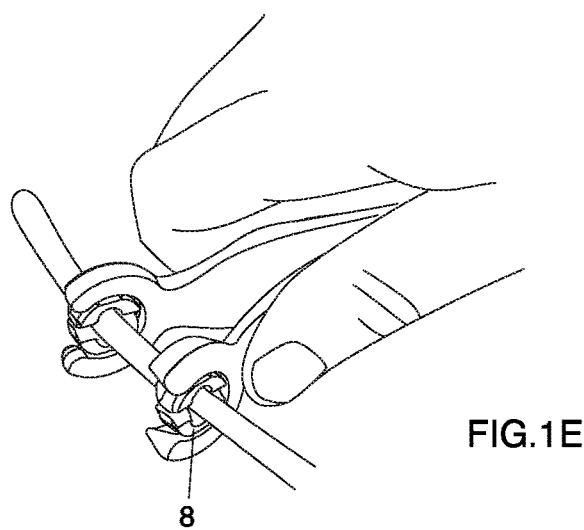
FIG. 1E is a perspective view of the device of FIG. 1A. This view also illustrates how the device may be handled by the operator.
Figure 4A:
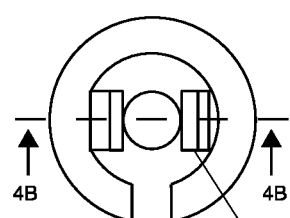
FIGS. 4A and 4B are illustrations of an embodiment of a one-way gripping valve in which there is a single cam. The valve is shown in a relaxed state.
Figure 4B:
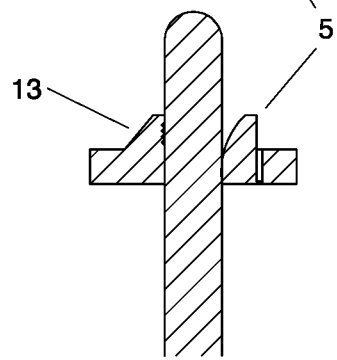
Figure 4C:
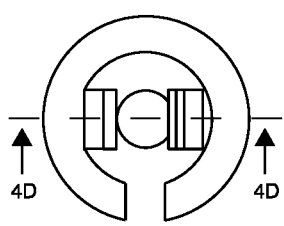
FIGS. 4C to 4E illustrate the valve of FIG. 4A (in which there is a single cam and an abutment) in a gripping state. The views are plan, cross-sectional and perspective respectively.
Figure 4D:
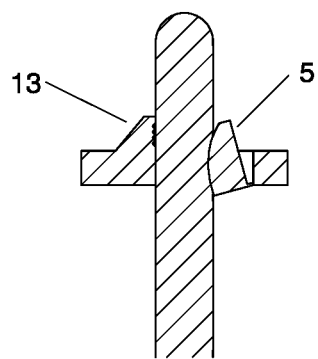
Figure 4E:
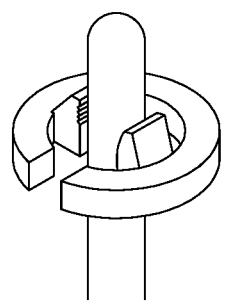

Referring to FIGS. 1A to 1D, a first embodiment of an insertion device (e.g., a catheter insertion device) is illustrated. It includes a first one-way gripping valve 1 and a second one-way gripping valve 2 attached to a proximal handle 3 (a first arm) and distal handle 4 (a second arm), respectively, at the distal end of each arm/handle. First arm 3 and second arm 4 are joined at hinge region 9 at their proximal ends. In this example, a bias (e.g., Biasing mechanism 10) biases hinge region 9 so as to increase the distance between the two valves. Each valve comprises two cams 5, each of which is attached to a valve frame 6 by a cam hinge 7. Each valve (e.g., in this example, the cams 5 forming part of each valve) has a groove 8 which is designed to prevent catheter 12 from sliding off-axis during use. During manufacture, hinge region 9 may be opened such that first arm 3 and second arm 4 are angled at or about 180 degrees to each other. In this way, the device may be manufactured by injection molding in a single piece. After injection molding the apparatus may be flexed at hinge region 9 in preparation for use. Second arm 4 and first arm 3 are shown to be shaped in such a way that it is apparent to the operator in which direction the device is to be gripped, as illustrated in FIG. 1E. For example, second arm 4 may have a concavity on its distal surface which readily and comfortably fits the thumb of the operator, and first arm 3 may have a convexity 11 to which the operator's fingers comfortably conform. In this embodiment, it is natural to grasp the device in such a way that the catheter moves away from the operator, in a proximal direction.

In said preferred embodiment, the catheter is mounted by inserting its proximal tip through the distal side of the first valve and advanced in a proximal direction until it is disposed within the nip of both valves.

In an alternative embodiment, (not shown), designed for patients who self-catheterize, the desired direction of movement of the catheter is towards the operator, (who is also the patient). In this embodiment, the orientation of the valves with respect to the arms/handles would be opposite to that described above, so that when the device fits into the operator's hand easily, the device would be oriented in such a way that the movement of the catheter would be towards the operator. For example, the one-way gripping valves in a variation such as shown in FIG. 1C may be oriented so that operation of the hand-held device advances the catheter into the patient, rather than away from the patient.

The distal side of the distal valve (first valve) intended for insertion of the catheter may be labelled as such.

The general way in which two reciprocating, coaxial valves can achieve movement of a catheter is illustrated in FIGS. 2A and 2B. FIG. 2A illustrates the approximation phase. In this phase, proximal valve 1 is in the relaxed state and allows free passage of the catheter in a proximal direction with respect to itself. During this phase, distal valve 2 is in the gripping state. FIG. 2B illustrates the distancing phase, during which proximal valve 1 is gripping and distal valve 2 is relaxed, allowing movement of the catheter in a proximal direction. In FIGS. 2A and 2B a cam cleat type valve is utilized for the illustration, but the principle is generalizable to other embodiments of valve, examples of which will be described below.

Each valve comprises one or more catheter-contact elements and a housing or frame. The valve allows passage of the catheter in one axial direction only. Each catheter-contact element has at least one catheter-contact surface, which may be ridged, grooved or otherwise textured to modify the frictional force between it and the catheter. Various embodiments of valves are described below.

FIGS. 3A to 3F illustrate an embodiment of a valve which is conceptually very much like a cam cleat commonly used to secure lines on sailboats. It employs two opposed cams 5, each of which is pivotally attached to a frame 6 by a cam hinge 7. Each cam has an arcuate catheter-contact surface for gripping the catheter. These catheter-contact surfaces are non-concentric with respect to their respective pivot axes. This causes the distance between the two catheter-contact surfaces—called the 'nip' in a cam cleat—to change as the cams pivot about their axes. When each cam pivots so that its catheter-contact surface moves in a substantially proximal direction the nip increases in size, allowing substantially free movement of the catheter in a proximal direction. When the cams pivot in the opposite direction, the nip closes and grips the catheter, impeding movement of said catheter. The cams are biased into a position such that their catheter-contact surfaces will exert sufficient force on any mounted, appropriately-sized catheter, so that attempted distal movement of said catheter will, by the power of the friction between it and the catheter-contact surfaces, cause the cams to pivot and further decrease the size of the nip. In this way the greater the distal motive force on a catheter, the greater is the grip of the valve impeding movement.

In order to prevent inadvertent demounting of the catheter from the nip, each cam may have a central groove on its catheter-contact surface (not shown).

FIGS. 4A to 4E illustrate an alternative embodiment of a valve in which a single cam 5 is used to grip the catheter by pressing it against an abutment 13.

Figures 5A, 5B:
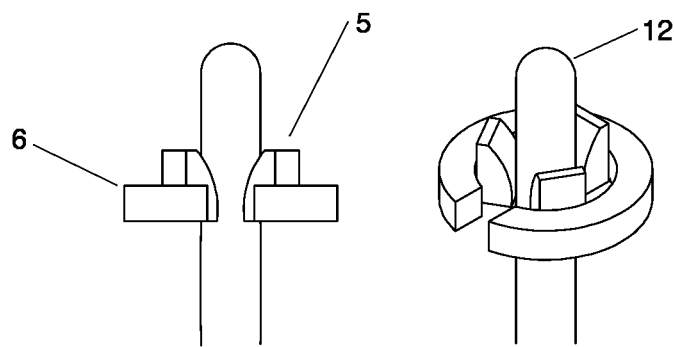
FIGS. 5A and 5B are elevation and perspective views, respectively, of an embodiment of a one-way gripping valve with three cams shown in a relaxed state.

FIGS. 5A and 5B illustrate an alternative embodiment of a valve in which three cams 5 are pivotally attached to a valve frame 6. Similarly, as many cams as may fit into the valve frame may be used.

Figures 6A, 6B:
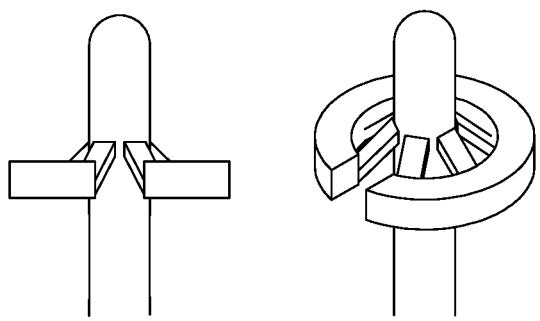
FIGS. 6A and 6B are elevation and perspective views, respectively, of an embodiment of a one-way gripping valve in which the catheter-contact elements are members extending from the valve frame in a radially inward (e.g., centripetal) and proximal direction.

FIGS. 6A and 6B illustrate an alternative embodiment of a valve in which the catheter-contact elements consist of elongate members attached around the valve frame and protruding in a proximal and centripetal direction, where they contact the catheter. Although their catheter-contact surfaces may not be cam-shaped, it can be readily appreciated by a person having ordinary skill in the art that this embodiment could allow proximal movement of a catheter and impede distal movement of the same if each catheter contact member has the correct amount of resilience and strength.

Figure 7A:
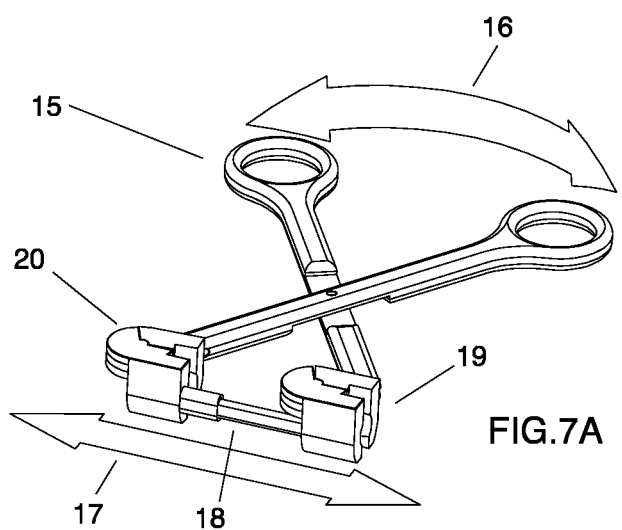
FIGS. 7A and 7B are perspective and plan views, respectively, of an embodiment of a hand-operated catheter advancement device in which the state of the one-way gripping valves (gripping or relaxed) is determined by the movement of the reciprocation device.
Figure 7B:
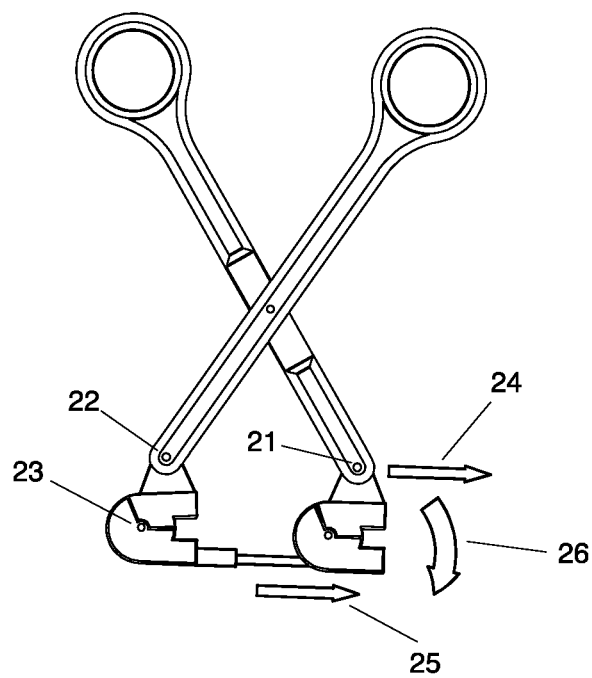

FIGS. 7A and 7B illustrate an alternative embodiment of the apparatus in which each the state of each valve, (gripping or relaxed), is mechanically determined by the force exerted onto the valve by the reciprocation mechanism. Each valve consists of two jaws which are rotationally attached to each other at jaw hinge 23. The lower jaws, (those not directly attached to the reciprocation mechanism), are slidingly attached to each other by alignment shaft 18, which restrains the movement of the two valves in a coaxial relationship (arrow 17). The upper jaws are rotationally attached to the reciprocation mechanism at hinges 21 and 22. In this embodiment a scissor reciprocation mechanism is illustrated, but the same principle can apply with many other reciprocation mechanisms. Arrow 16 indicates reciprocal motion of the handles 15.

During the approximation phase a proximal motive force is applied to the distal valve 20 via hinge 21 and a distal motive force is applied to the proximal valve 19 via hinge 21. This results in the distal valve entering the gripping state and the proximal valve entering the relaxed state. During the distancing phase (arrow 24) a proximal motive force is applied to the proximal valve at hinge 21 (arrow 25) and a distal motive force is applied to the distal valve at hinge 22. This results in gripping of the catheter at the proximal valve (arrow 26) and relaxation of the distal valve.

A person having ordinary skill in the art will appreciate that there are many more mechanical mechanisms possible that will achieve the same effect on the valves without departing from the scope.

FIGS. 8A to 8C illustrate an alternative embodiment of a one-way gripping valve in which the catheter-contact elements consist of one or more sliding plugs 27 enclosed in a housing 29. The sliding plugs are biased in a centripetal and distal direction by biasing springs 28, where they make contact with catheter 12. The interaction of the shapes of the plugs and housing is such that if the plugs move distally they will also exert more pressure on the catheter and impede its movement. A proximal force on the catheter will, by friction between the catheter and the plug, move the plug or plugs in a proximal and centrifugal direction, thereby allowing further movement of the catheter in a proximal direction. In FIG. 8B the plug is shown as wedge-shaped, but a variety of shapes is possible which will achieve the same end, for example, conic sections.

FIGS. 9A to 9D illustrate an alternative embodiment of a one-way gripping valve in which a roller mechanism allows one-way movement of the catheter. Roller 30 is constrained in its movement by guide slot 31 in housing 32 and biased in a centripetal-distal direction by a biasing mechanism (not shown). A person with ordinary skill in the art can appreciate that this embodiment will allow proximal movement of the catheter and impede distal movement.

An alternative embodiment, (not illustrated), of a one-way gripping valve mechanism employs one or more roller drums which compress and grip the catheter with their respective catheter-contact surfaces. A ratcheting mechanism allows each roller drum to rotate in one direction only, thereby creating a valve.

In order to increase the range of catheter diameters over which a valve will function, valves may use a mechanism to exert centripetal force on the catheter-contact elements. This would have the effect of narrowing the nip so that small-diameter catheters will engage the catheter-contact surfaces.

FIGS. 10A and 10B illustrate an embodiment of this biasing mechanism in which the valve frame has a hinge 34 which allows limited opening of the nip. This may also act as a release structure (e.g., demounting gap). In this variation the demounting gap is gated by the frame, which is hinged 34 to open/close based on the pressure applied. Biasing spring 33 biases the frame and nip towards a closed position (e.g., closing the gate, preventing demounting). FIGS. 11A and 11B illustrate an alternative embodiment in which the cam hinge 35 also acts as a biasing spring exerting centripetal pressure onto the cam.

Figures 12A, 12B:
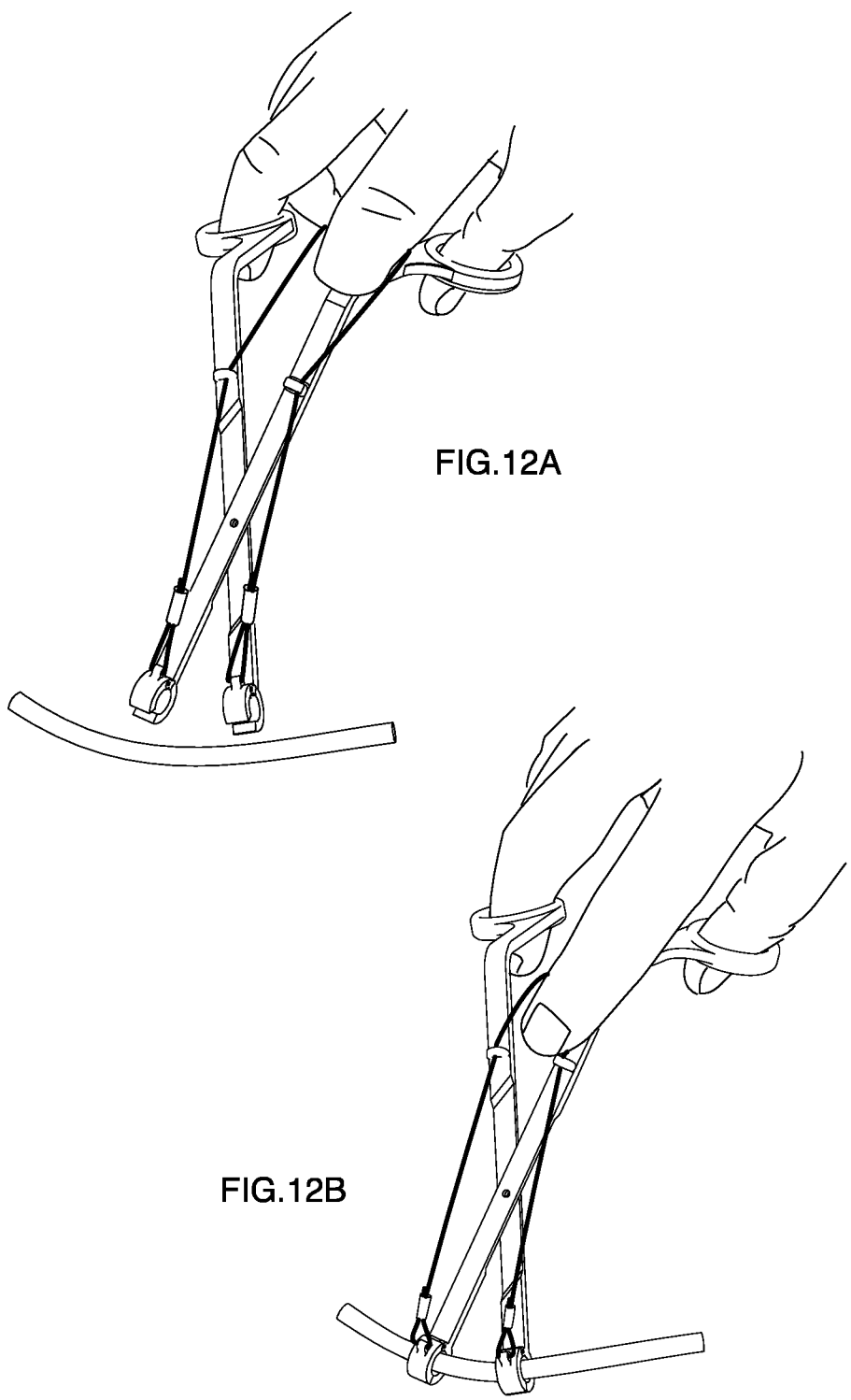
FIGS. 12A and 12B are perspective views of an embodiment in which the one-way gripping valves are able to be opened and/or closed mechanically from a distance.

FIGS. 12A and 12B illustrate an example of a mechanism for opening and closing the valves at a distance. In this example each valve may include a demount gap formed in the frame partially surrounding the one-way gripping valves; the gate is configured to be opened or closed to open or close the demount gap. The gate actuator is configured to open or close the gate via a control coupled to one or both of the first and second arms, as shown. The embodiment shown in FIGS. 12A and 12B comprises valves having a demount gap that is gated or biased into a closed position (FIG. 12B—biasing mechanism not shown) and opened by traction on a cable (FIG. 12A); the cable is a gate actuator and may also be (as shown in FIG. 12A) a control that can be operated to open the demounting/mounting gap. A mechanism such as this would be useful, for example, in an anaesthetized patient, when an NGT has been advanced through the nose as far as the pharynx. The valves could then be introduced to the pharynx through the patient's mouth and opened to mount the catheter, then closed once the catheter is mounted. The device could be operated by the operator's hand (outside the mouth) to advance the catheter into the stomach via the esophagus. When the task is completed, the valves could be opened once again to demount the catheter. Similarly, a device could be envisioned which mounts a catheter inside a body space (e.g. the abdominal cavity), for cannulation of a duct (e.g. the biliary duct). Instead of a cable, one or more push-rods or pull-rods may be used, with or without one or more biasing mechanisms, to open and/or close the valves. A person having ordinary skill in the art will appreciate that there are many more mechanical mechanisms possible that will achieve the same opening and closing effect on the demounting gap of the valves without departing from the scope of the invention.

Many mechanisms are possible which can effect reciprocal motion of the valves. Some of the possible embodiments are described below.

Figure 13A:
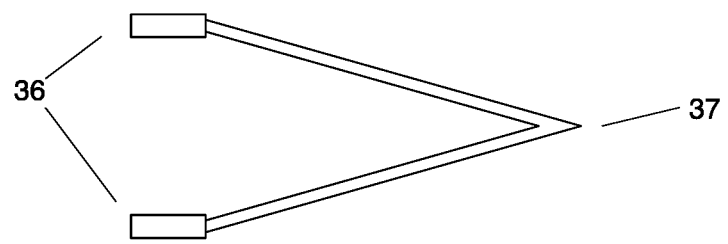
FIG. 13A is a view of an embodiment of a reciprocation mechanism, shown as a pair of hinged arms which function much like tweezers.
Figure 13B:
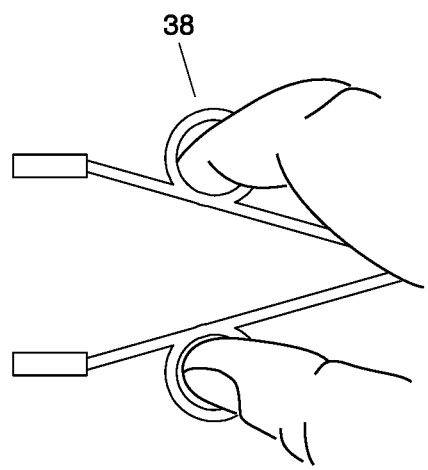
FIG. 13B is a view of an embodiment of a reciprocation mechanism which functions much like tweezers and also comprises includes finger holes.

FIGS. 13A and 13B illustrate an embodiment of a reciprocation mechanism in which first and second arms (e.g., proximal and distal handles) are flexibly attached at one end to each other in a hinge region 37 and at their other ends to their respective valves 36. Their attachment to each other (hinge region 37) may act as a biasing spring, biasing the valves into either approximation or distancing phases. FIG. 13B illustrates an embodiment which includes finger holes 38. The use of finger holes would allow the operator to exert approximation force, distancing force, or both.

Figure 14A:
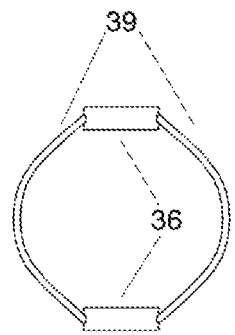
FIGS. 14A and 14B are plan and perspective views of an embodiment of a reciprocation mechanism in which two valves are biased apart and joined by two diametrically-opposed springs.
Figure 14B:
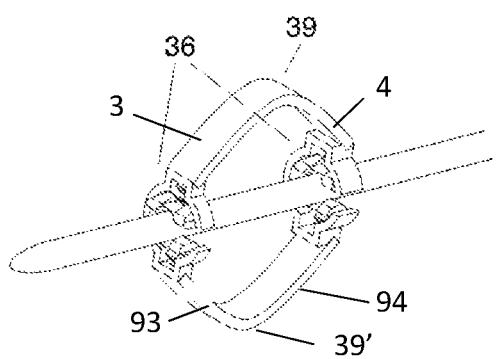

FIGS. 14A and 14B illustrate an alternative embodiment of a reciprocation mechanism which comprises hinge regions 39, 39' that each operate as biasing springs, each attached at each end to the valves 36 via a first 3 and second 4 arm or a third 93 and fourth 94 arm. Exertion of a centripetal force on the convexities of each hinge region (e.g., biasing spring) will cause the valves to move further apart from each other. Relaxing the said force will allow them to return to their former position.

Figure 15:
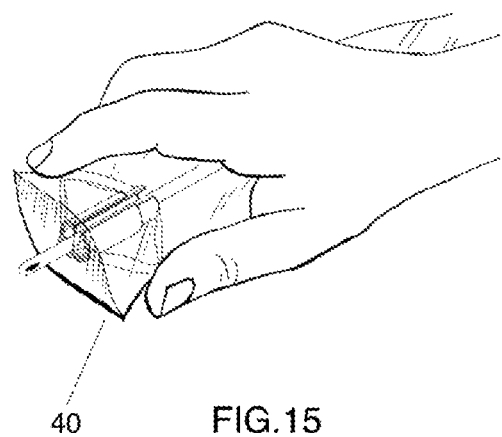
FIG. 15 is a perspective view of an embodiment of a hand-operated catheter advancement device being operated through a sterile catheter package.

FIG. 15 illustrates how the reciprocation mechanism in FIGS. 14A and 14B can be used to advance a catheter from inside a sterile bag 40 without touching either the device for advancing the catheter or the catheter.

Figure 16:
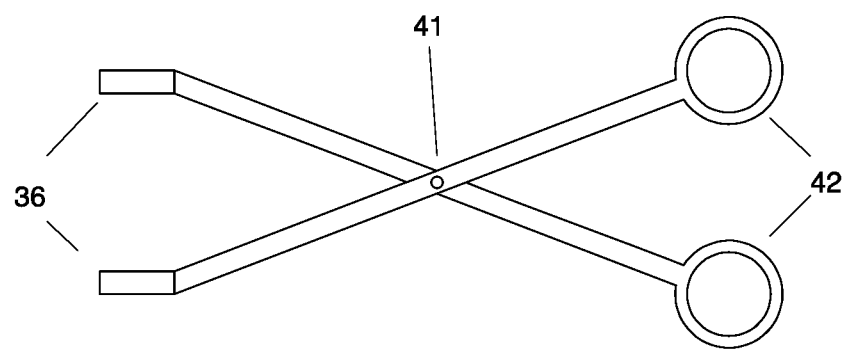
FIG. 16 is a view of a reciprocating hand-operated catheter advancement device in which the handles operates like a scissors. In this embodiment, as the finger holes move closer to each other, the valves move closer to each other.
Figure 17:
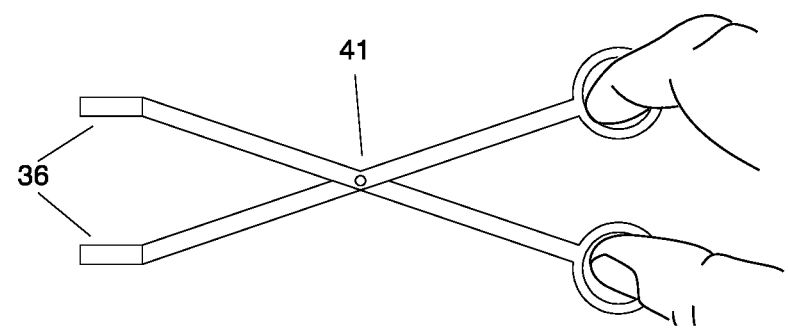
FIG. 17 is a view of a reciprocation hand-operated catheter advancement device in which the handles operate like a scissors but where the hinge is reversed compared to FIG. 16. As the finger holes come closer to each other, the one-way gripping valves move farther apart from each other.

FIGS. 16 and 17 illustrate alternative embodiments of reciprocation mechanisms which use a scissor mechanism with a hinge region (hinge 41). In FIG. 16 approximation of finger holes 42 causes approximation of the valves 36, and distancing of the finger holes causes distancing of the valves 36. In FIG. 17 the embodiment illustrated has a different hinge arrangement, so that approximation of the finger holes causes distancing of the valves and vice versa.

Figure 18B:
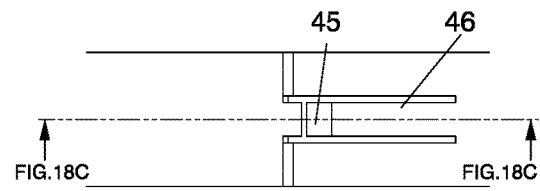
FIGS. 18A to 18G are illustrations of an embodiment of a spring mechanism connecting the first and second forceps handles of one variation of a hand-operated catheter advancement device such as the one shown in FIG. 1A.
Figure 18A:
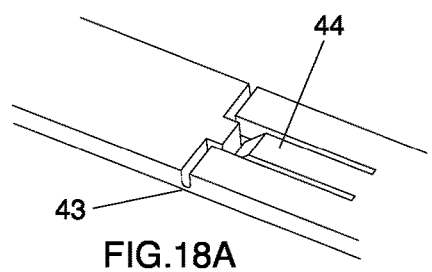
Figure 18C:
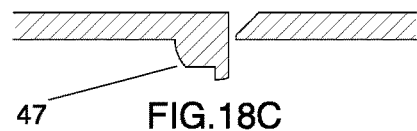
Figure 18D:
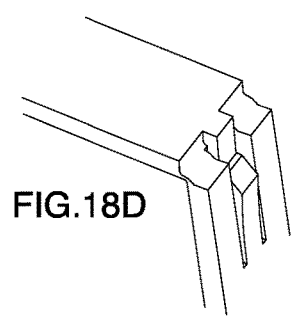
Figure 18E:
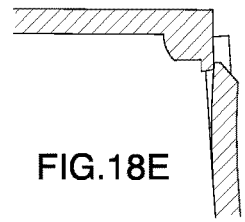
Figure 18F:
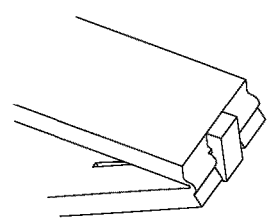
Figure 18G:
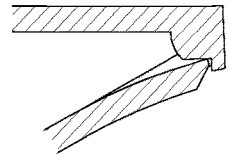

A preferred reciprocation mechanism embodiment is illustrated in FIGS. 18A to 18G. This embodiment would allow for injection molding of the apparatus in a single piece. It comprises a living hinge 43, a protruding member 47 and a biasing spring 44. Biasing spring 44 comprises a body 46, which is connected at one end to one of the handles, and a tip 45. Together, biasing spring 44 and protrusion 47 act as a latch. Protrusion 47 is shaped such that as the hinge is folded into its functional position, it makes contact with, and causes to flex, biasing spring 44 (FIGS. 18D and 18E). When in the functional position, (FIGS. 18F and 18G), biasing spring 44 biases the hinge towards a more open position but the latch comprising tip 45 and protruding member 47 prevents re-opening of the hinge. In the approximation phase, biasing spring 44 resists approximation of the valves and in the distancing phase recoil of biasing spring 44 acts to distance the valves from each other.

Many designs will facilitate demounting of the catheter from the device. Some of the possible embodiments are described below.

Figures 19A, 19B:
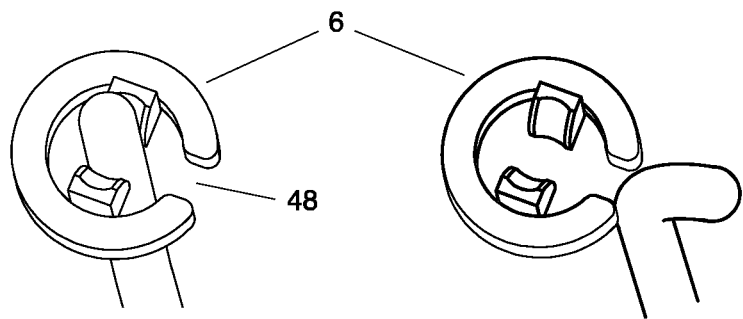
FIGS. 19A and 19B are perspective illustrations of a one-way gripping valve including a demount mechanism in which the catheter may be demounted (e.g., removed) from the valve via a demount gap in the valve frame.

FIGS. 19A and 19B illustrate an embodiment in which the catheter is held in place by grooves in the catheter-contact surfaces of the cams. The compressibility of the catheter allows it to be removed through a demount gap 48 in the valve frame 6 by application of a centrifugal force on the catheter.

Figures 20A, 20B:
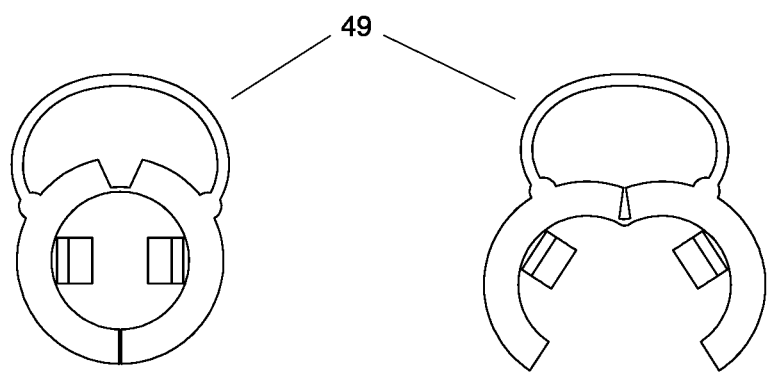
FIGS. 20A and 20B are plan views of a demount gap in which a spring holds the valve frame closed (FIG. 20A) or open (FIG. 20B) depending on the degree to which the valve frame is opened or closed.

FIGS. 20A and 20B illustrate an embodiment of the advancement device in which a spring 49 biases a hinged valve frame into a closed position with sufficient force to allow functioning of the valve. This force can be manually overcome in order to open the frame for demounting of the catheter.

Figures 21A, 21B:
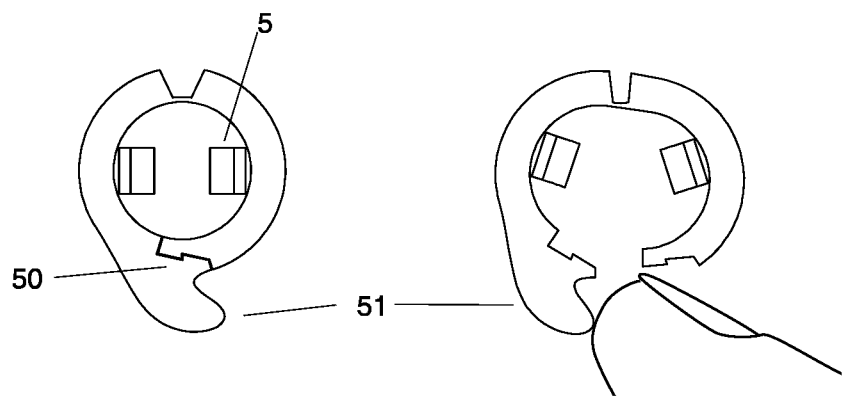
FIGS. 21A and 21B are plan views of an embodiment of a demount gap in which a fastener (e.g., shown as a snap in this example) holds the frame closed (FIG. 21A) until the fastener is released (FIG. 21B).

FIGS. 21A and 21B illustrate an embodiment of the advancement device in which the valve frame is hinged at one point and held closed by a snap 50 at another. A force applied to tab 51 can disengage the snap and allow the valve frame to flex open for demounting of the catheter from the valve.

Figures 22A, 22B:
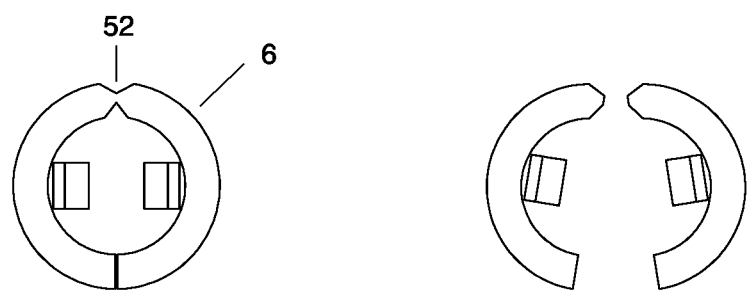
FIGS. 22A and 22B are plan views of an embodiment of a demount mechanism in which the valve frame breaks open to release the catheter.

FIGS. 22A and 22B illustrate an embodiment of the advancement device in which a section or sections of the valve frame can be broken at weak point 52 in valve frame 6 to allow demounting of the catheter from the valve.

Figure 23:
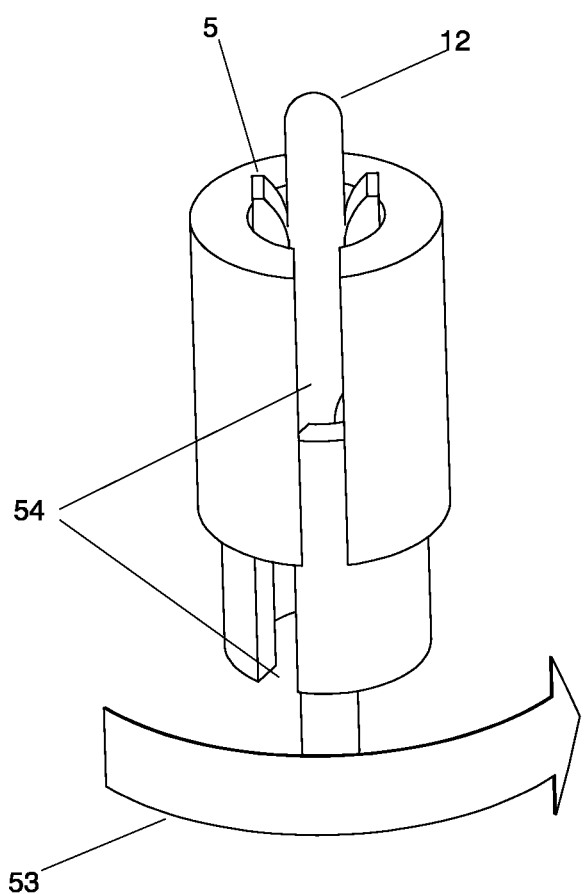
FIG. 23 is a perspective view of an embodiment of a demount mechanism in which each valve is integrated with an incomplete cylinder, one of which slides within the other. The demount gap in each cylinder wall is angularly offset from the other but the cylinders can be twisted with respect to each other to align the gaps. Thus, the demount mechanism may be fastened shut or opened.
Figure 25A:
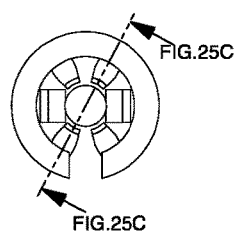
FIGS. 25A to 25D are plan, elevation, cross-sectional and perspective views of an embodiment an anti-buckling enclosure for a hand-operated catheter advancement device in which one or more elongated members are attached to one valve and extend adjacent to the catheter towards the other valve, where it or they pass between the contact elements of the valve.
Figure 25B:
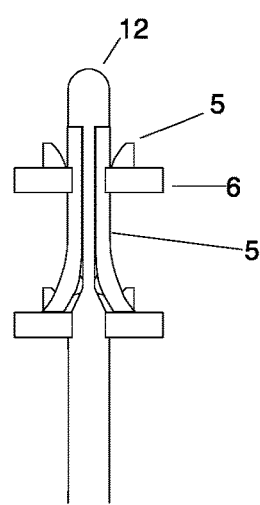
Figure 25C:
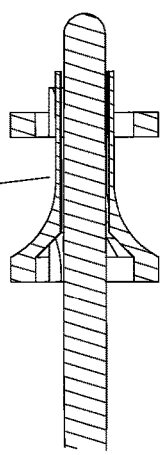
Figure 25D:
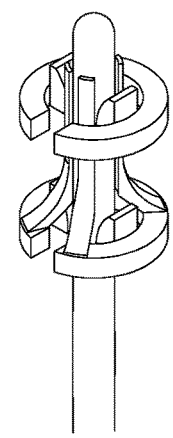

FIG. 23 illustrates an embodiment of the advancement device in which each valve is elongated in an axial direction and one of them can slide within the other. Each has a demount gap 54 through which the catheter 12 may be demounted. Said demount gaps are ordinarily angularly offset but the valve frames can be twisted with respect to each other (arrow 53) so that the catheter can be demounted when the gaps are aligned.

Some embodiments of the advancement device which comprise anti-buckling mechanisms are described below.

FIGS. 24A to 24D illustrate an embodiment of the advancement device in which cylindrical elongations of each valve frame form a guide which prevents buckling of the catheter.

FIGS. 25A to 25D illustrate an embodiment of the advancement device in which guide members 57 protrude from one valve frame and extend towards the other, where they may extend between the catheter-contact elements 5. Their proximity to the catheter provides support to prevent buckling. Alternatively, guide members may extend from each valve towards the other and attach slidingly to each other (not shown).

An alternative embodiment, (not illustrated), includes a light-source for illumination of the relevant bodily orifice.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A catheter advancement device comprising:
   a first one-way gripping valve at a distal end of a first arm, wherein the first one-way gripping valve is configured to allow a catheter to move in a first direction through an opening of the first one-way gripping valve while preventing the catheter from moving in a second direction that is opposite from the first direction;
   a second one-way gripping valve at a distal end of a second arm, wherein the second one-way gripping valve is configured to allow the catheter to move in the first direction through an opening of the second one-way gripping valve while preventing the catheter from moving in the second direction; and
   a hinge region connecting the first arm to the second arm at an angle so that the opening of the first one-way gripping valve is approximately coaxially disposed with the opening of the second one-way gripping valve;
   wherein the hinge region is configured to allow the first arm to move relative to the second arm to reciprocate the one-way gripping valve and the second one way gripping valve to advance the catheter.

2. The device of claim 1, further comprising a demount gap in at least one of the first one-way gripping valve and the second one-way gripping valve, through which the catheter may demount from the device.

3. The device of claim 2, wherein the demount gap comprises a gap formed in a frame partially surrounding the first one-way gripping valve.

4. The device of claim 2, further comprising a gate configured to be opened or closed to open or close the demount gap.

5. The device of claim 4, further comprising a gate actuator configured to open or close the gate via a control coupled to one or both of the first and second arms.

6. The device of claim 1, further comprising a third arm connected to the first one-way gripping valve, a fourth arm connected to the second one-way gripping valve, and a second hinge region connecting the third arm to the second arm.

7. The device of claim 1, wherein the hinge region connects the first arm to the second arm at an angle of between 5 degrees and 180 degrees.

8. The device of claim 1, wherein one or both of the first one-way gripping valve and the second one-way gripping valve comprises one or more cams.

9. The device of claim 1, wherein one or both of the first one-way gripping valve and the second one-way gripping valve comprises two or more cams.

10. The device of claim 1, wherein the hinge region connects the first arm to the second arm so that the opening of the first one-way gripping valve is coaxially within +/−20 degrees of the opening of the second one-way gripping valve.

11. The device of claim 1, further comprising a guide enclosure extending from the first one way gripping valve, towards the second one-way gripping valve to inhibit buckling of the catheter during advancement.

12. The device of claim 1, wherein the hinge region comprises a living hinge.

13. A catheter advancement device comprising:
   a first one-way gripping valve at a distal end of a first arm, wherein the first one-way gripping valve is configured to allow a catheter to move in a first direction through an opening of the first one-way gripping valve while preventing the catheter from moving in a second direction that is opposite from the first direction;
   a second one-way gripping valve at a distal end of a second arm, wherein the second one-way gripping valve is configured to allow the catheter to move in the first direction through an opening of the second one-way gripping valve while preventing the catheter from moving in the second direction;
   a hinge region connecting the first arm to the second arm at an angle of between 10 degrees and 180 degrees;
   wherein the hinge region is configured to allow the angle between the first arm and the second arm to change and reciprocate the first one-way gripping valve and the second one way gripping valve to advance the catheter; and
   a demount gap in the first one-way gripping valve through which the catheter may demount from the first one-way gripping valve.

14. The device of claim 13, further comprising a second demount gap in the second one-way gripping valve through which the catheter may demount from the device.

15. The device of claim 13, wherein the demount gap comprises a gap formed in a frame partially surrounding the first one-way gripping valve.

16. The device of claim 13, further comprising a gate configured to be opened or closed to open or close the demount gap.

17. The device of claim 16, further comprising a gate actuator configured to open or close the gate via a control coupled to one or both of the first and second arms.

18. The device of claim 13, further comprising a third arm connected to the first one-way gripping valve, a fourth arm connected to the second one-way gripping valve, and a second hinge region connecting the third arm to the fourth arm.

19. The device of claim 13, wherein one or both of the first one-way gripping valve and the second one-way gripping valve comprises one or more cams.

20. The device of claim 13, further comprising a guide enclosure extending from the first one way gripping valve, towards the second one-way gripping valve to inhibit buckling of the catheter during advancement.

21. The device of claim 13, wherein the hinge region comprises a living hinge.

22. A catheter advancement device comprising:
a first one-way gripping valve at a distal end of a first arm, wherein the first one-way gripping valve is configured to allow a catheter to move in a first direction through an opening of the first one-way gripping valve while preventing the catheter from moving in a second direction that is opposite from the first direction;
a second one-way gripping valve at a distal end of a second arm, wherein the second one-way gripping valve is configured to allow the catheter to move in the first direction through an opening of the second one-way gripping valve while preventing the catheter from moving in the second direction;
a living hinge region connecting the first arm to the second arm at an angle of between 10 degrees and 180 degrees;
wherein the hinge region is configured to allow the angle between the first arm and the second arm to change to reciprocate the first one-way gripping valve and the second one way gripping valve to advance the catheter;
a first demount gap in the first one-way gripping valve through which the catheter may demount from the first one-way gripping valve; and
a second demount gap in the second one-way gripping valve through which the catheter may demount from the second one-way gripping valve.

* * * * *